(12) United States Patent
Lang

(10) Patent No.: US 8,755,859 B2
(45) Date of Patent: Jun. 17, 2014

(54) MEDICAL ELECTRODE WITH PRINTED SHIELDED FEED LINE

(71) Applicant: Burrhus Lang, Innsbruck (AT)

(72) Inventor: Burrhus Lang, Innsbruck (AT)

(73) Assignee: Leonh. Lang, Innsbruck (AT)

( * ) Notice: Subject to any disclaimer, the term of this patent is extended or adjusted under 35 U.S.C. 154(b) by 0 days.

(21) Appl. No.: 13/929,959

(22) Filed: Jun. 28, 2013

(65) Prior Publication Data

US 2013/0289376 A1 Oct. 31, 2013

Related U.S. Application Data

(63) Continuation of application No. PCT/AT2011/000496, filed on Dec. 15, 2011.

(30) Foreign Application Priority Data

Jan. 3, 2011 (AT) .................................. A 004/2011

(51) Int. Cl.
*A61B 5/04* (2006.01)
*A61B 5/0408* (2006.01)

(52) U.S. Cl.
USPC ............................. 600/372; 600/382; 600/393

(58) Field of Classification Search
CPC .............. A61B 5/0408; A61B 5/0478; A61B 5/04085; A61B 2562/182; A61B 2562/222
USPC ........................ 600/372, 382, 391, 392, 393
See application file for complete search history.

(56) References Cited

U.S. PATENT DOCUMENTS

| 4,353,372 | A | 10/1982 | Ayer |
| 4,442,315 | A | 4/1984 | Segawa |
| 4,539,995 | A * | 9/1985 | Segawa .......................... 600/385 |
| 5,337,748 | A | 8/1994 | McAdams et al. |
| 6,434,410 | B1 | 8/2002 | Cordero et al. |
| 7,512,449 | B2 | 3/2009 | Lang et al. |
| 7,826,882 | B2 * | 11/2010 | McIntire et al. .............. 600/393 |
| 7,957,785 | B2 | 6/2011 | Nishimura |

(Continued)

FOREIGN PATENT DOCUMENTS

| DE | 4091800 C2 | 9/2000 |
| DE | 69923680 T2 | 3/2006 |

(Continued)

OTHER PUBLICATIONS

Austrian Patent Application No. A 4/2011 Search Report dated Jun. 17, 2011.

(Continued)

*Primary Examiner* — Lee S Cohen
(74) *Attorney, Agent, or Firm* — Novak Druce Connolly Bove + Quigg LLP

(57) ABSTRACT

The invention relates to a medical electrode (1) comprising an electrode head (2) and an electric feed line (3) to the electrode head (2), said teed line (3) having an electrically conductive shielding layer (4), a dielectric element (5), and an electric conductor (6). The feed line (3) has an elongate substrate element (7) onto which the electrically conductive shielding layer (4) is at least partly printed. The at least partly printed shielding layer (4) entirely surrounds the dielectric element (5) and the electric conductor (6) transversely to the longitudinal axis (L) of the feed line (3). The shielding layer comprises an upper (4a) and a lower (4b) shielding ply.

14 Claims, 4 Drawing Sheets

(56) References Cited

U.S. PATENT DOCUMENTS

| | | |
|---|---|---|
| 2007/0299471 A1 | 12/2007 | Takahashi et al. |
| 2008/0249389 A1* | 10/2008 | Haug et al. .................. 600/372 |
| 2010/0030167 A1 | 2/2010 | Thirstrup et al. |
| 2010/0139943 A1 | 6/2010 | Abe et al. |
| 2010/0198044 A1 | 8/2010 | Gehman et al. |

FOREIGN PATENT DOCUMENTS

| | | | |
|---|---|---|---|
| EP | 1752093 | A2 | 2/2007 |
| JP | 2008212487 | A | 9/2008 |
| WO | WO2004054442 | A1 | 7/2004 |
| WO | WO2009007877 | A2 | 1/2009 |

OTHER PUBLICATIONS

International Application No. PCT/AT2011/000496 Search Report dated Mar. 21, 2012.

* cited by examiner

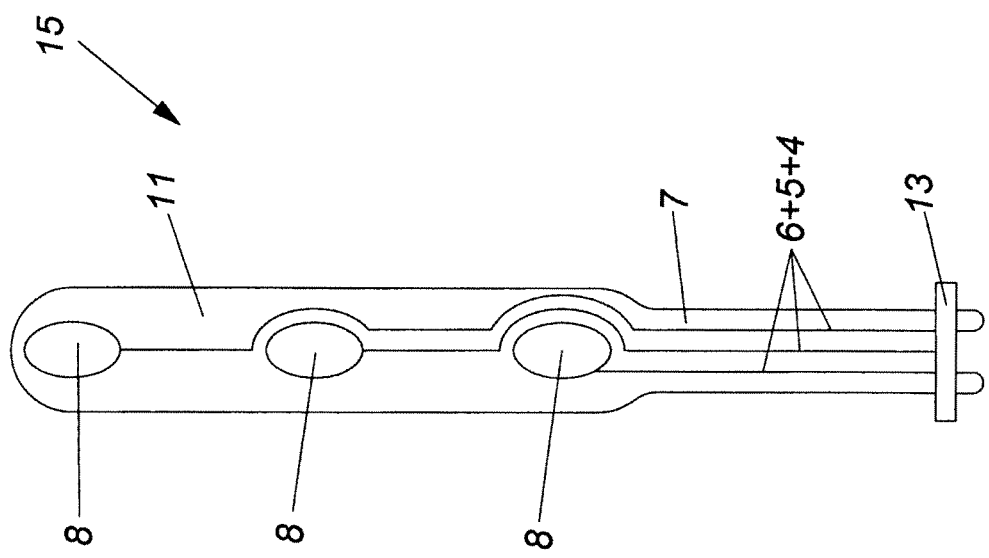
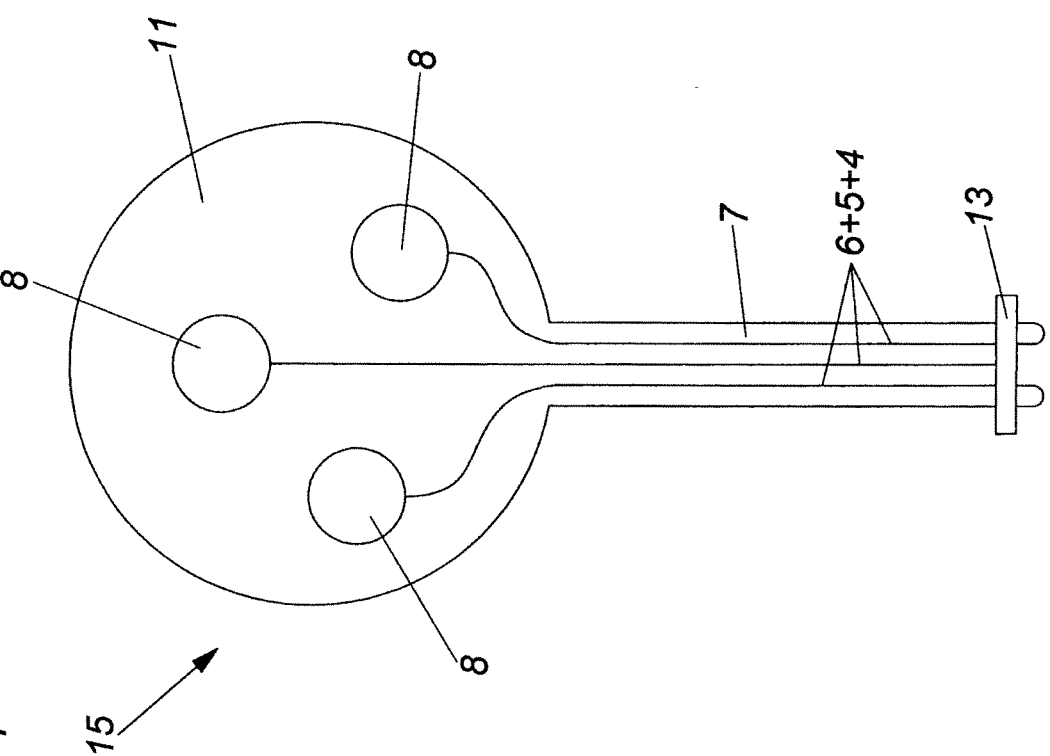

MEDICAL ELECTRODE WITH PRINTED SHIELDED FEED LINE

PRIORITY INFORMATION

This application is a continuation application of PCT/AT2011/000496, filed Dec. 15, 2011, which claims priority to Austrian Patent Application No. A 4/2011 filed Jan. 3, 2011, the disclosures of which are incorporated herein by reference in their entirety.

FIELD OF THE INVENTION

The invention relates to a medical electrode with an electrode head and an electric feed line to the electrode head, wherein the feed line has an electrically conductive shielding layer, a dielectric element and an electric conductor, wherein the feed line has an elongated substrate element onto which the electrically conductive shielding layer is at least partly printed, and also relates to a method for producing such a medical electrode.

BACKGROUND OF THE INVENTION

Medical electrodes for introducing and discharging electric currents into and from the human or animal body have been known for a considerable length of time. A very wide range of production methods also exists in this field, in which connection it has become increasingly important in recent years to produce electrodes that are as small and light as possible. In the field of diagnostic electrodes there is also increasingly a desire to allow evaluations that are uninfluenced as far as possible by electromagnetic radiation and other sources of interference. To this end, in addition to corresponding electrode designs shielded cables in particular are used. These shield the detected signal against interference by electromagnetic radiation and possibly also protect the patient.

In order in particular to produce the electrode head—with which the medical electrode is attached to the body—as simply and thinly as possible, it is known from the prior art to apply at least individual layers by a printing method. For example, US 2010/0030167 A1 shows an electrode with electrically conductive rings and a further shielding layer as second electrically conductive layer. This second electrically conductive layer can be printed onto the electrode.

According to WO 2009/007877 A2 an electrode head is principally described, in which a conductive ink is applied to the surface of a film layer. It can also be envisaged to print a dielectric layer over a base conductor.

Furthermore it is known from DE 699 23 680 T2 that in the case of an electrode a sealing layer (in the chemical sense) of a silver alloy ink is printed over a circuit of conductive ink.

Furthermore DE 40 91 800 C2 shows a biosignal electrode onto which a two-ply electrically conductive layer is printed.

In the technical field of the feed line to the electrode head, shielded and unshielded cables of round cross-section are known. For a connection that integrates the electrode head into the shielding, the connections and associated plugs either have to be configured in a relatively complicated manner, as is illustrated in EP 1 569 551 B1, or the plug additionally has to be designed as a shield overlapping the electrode head, which means that this region is heavy and inflexible and moreover is qualitatively inferior to a shielding integrated into the electrode.

The disadvantage therefore is basically the fact that the production of a medical electrode with an electrode head and integrated, unshielded and round cable feed line is carried out in a series of steps that are always very complicated, expensive and normally completely separate from one another, involving to some extent manual assembly, which is why the processes for producing such medical electrodes are very inefficient.

These difficulties—and therefore the costs—are magnified especially if only one electrode with a shielded electrode head and integrated shielded cable feed line is to be produced, which is why such single-use products are hardly ever found on the market.

Furthermore, as regards the feed line to the electrode head of a medical electrode it is known from U.S. Pat. No. 4,353,372 A that the electric conductor on the feed line as well as the conductor in the region of the connecting plug are printed as a conductive layer.

From U.S. Pat. No. 4,442,315 A and US 2007/0299471 A1 in each case medical electrodes with an electrode head and feed line are known, in which the shielding layers and insulating layer can be printed on in the region of the feed line. With these printed-on shielding layers there is however no complete shielding of the electric conductors, so that electromagnetic radiation or other sources of interference can influence the signals fed through the electric conductor in the feed line.

SUMMARY OF THE INVENTION

The object of the present invention is therefore to provide an improved medical electrode compared to the prior art. In particular the hitherto known (shielded) feed cables should be easier to handle. In addition the electrical connections between the electrode head and a medical evaluation or initiation unit should be able to be designed in a less complicated manner and produced more efficiently. Also, the signals transmitted via the electric conductor in the feed line should be unaffected as far as possible by sources of interference.

This object is achieved for a medical electrode with the features of the preamble of claim 1, in that the feed line comprises an elongated substrate element onto which the electrically conductive shielding layer is at least partly printed. Due to the fact that at least a part of the shielding is printed, a significantly simpler fabrication and a production of the medical electrode that more accurately matches the requirements can be achieved.

In order to achieve a particularly efficient and fast manufacture, it may particularly preferably be envisaged that also the dielectric element and/or the electric conductor are printed.

DETAILED DESCRIPTION OF THE INVENTION

An implementation variant may be envisaged in which the substrate element is implemented as a metalized film so that the substrate element already acts as a shield over certain regions. The electric conductor together with the dielectric are applied, preferably printed, onto this metalized film, and then first of all the printed part of the shield is printed on and is joined to the metalized film so that the electric conductor together with the dielectric is entirely surrounded transverse to the longitudinal direction of the feed line by the (two-part) shielding.

According to a particularly preferred embodiment of the present invention it may however also be envisaged that the electrically conductive shielding layer, the dielectric element and the electric conductor are printed, wherein preferably the shielding layer is printed at least partly directly onto the substrate element and the dielectric element and the electric conductor are printed indirectly onto the substrate element. This means that the dielectric element and the electric conductor do not directly contact the actual substrate, but are printed on top of one another in layers.

A feed line in the form of an at least partly printed "cable" can be improved if the feed line comprises an upper and a lower dielectric element that surrounds the electric conductor transverse to the longitudinal axis of the feed line. In order to achieve a feed line that is secure and is shielded all the way round, it is particularly preferred if the feed line comprises an upper and a lower printed shielding ply, wherein the upper and lower printed electric shielding ply surround the upper and lower printed dielectric element transverse to the longitudinal direction of the feed line.

The advantages of printing at least individual plies can be used not only for the feed line, but it is preferably also envisaged that the electrode head comprises an electrically conductive signal transmitting and receiving layer that is connected to the electric conductor of the feed line, a dielectric element that is connected to the dielectric element of the feed line, and a shielding layer that is connected to the shielding layer of the feed line, wherein at least the electrically conductive signal transmitting and receiving layer of the electrode head, the dielectric layer of the electrode head and/or the shielding layer of the electrode head are printed. At least two or all three of these components of the electrode head may also be printed.

For a particularly simple fabrication it may be envisaged in this connection that also the electrode head comprises an electrically non-conductive substrate element, wherein the shielding layer of the electrode head is printed directly onto the substrate element of the electrode head.

In principle it should also be possible for the substrate element to form the dielectric element, preferably the lower dielectric element. Accordingly no actual substrate element is necessary, but instead the necessary layers are simply printed directly or indirectly onto a dielectric element acting as substrate element.

In order to improve the patient's comfort, achieve a better protection against environmental influences and ensure a longer service life, it may preferably be envisaged that a protective layer, preferably consisting of plastic material, at least partly surrounds the electric feed line. Preferably this protective layer or coating layer completely encloses the other parts of the feed line transverse to the longitudinal direction of the feed line.

For a reliable and simple tapping and feeding of electric current, may preferably be envisaged that a connecting plug can be attached or mounted on the end of the feed line remote from the electrode head, via which the medical electrode can be connected to a medical evaluation and/or signal initiation unit. A particularly simple connectability to a connecting plug is possible by implementing the feed line with partly printed elements.

In principle it is of course possible for only individual regions or individual parts of the feed line and electrode head to be printed, though it is particularly preferably envisaged that the whole shielding layer, the whole dielectric element and/or the whole electric conductor between the electrode head and connecting plug is/are printed. This means that the shielding, dielectric element and electric conductor as well as the electrode head and also the feed line can be produced in a quick printing method involving only a few steps.

Protection is therefore also sought for a method having the features of claim 13. These steps are preferably implemented in the order specified in the claims. In order to be able to produce a feed line that is secure all the way round, further steps provide for the printing of an upper, dielectric element with the inclusion of the electric conductor onto the lower, dielectric element at least in the region of the feed line, wherein by means of the printing the upper and lower dielectric elements are cohesively connected at least over certain regions, and the printing of an upper, dielectric shielding ply with the inclusion of the upper and lower dielectric element onto the lower shielding ply at least in the region of the feed line, wherein by means of the printing the upper and lower shielding plies are cohesively connected at least over certain regions.

Such a production method is particularly suitable for producing a multiple electrode with at least two separate signal transmitting and receiving layers, wherein also at least two separate shielding layers, at least two separate dielectric elements and at least two separate electric conductors are printed onto a common substrate element. This substrate element can of course also be partly cut to size or cut into sections after the printing, so as to provide a greater compatibility with the feed line.

Further details and advantages of the present invention are described in more detail hereinafter with the aid of the description of the figures and with reference to the exemplary embodiments illustrated in the drawings, in which:

BRIEF DESCRIPTION OF THE DRAWINGS

FIGS. 7 and 8 are schematic views of multiple electrodes.

FIG. 1 shows a medical electrode 1, which comprises an electrode head 2, a feed line 3 and a connecting plug 13 (with in this case projecting pins 16). According to FIG. 1 the substrate element 7 of the feed line 3 and the substrate element 11 of the electrode head 2 are formed in one piece, onto which the shielding plies 4 and 10 are printed as the next layer. The dielectric elements 5 and 9 are then printed on, followed by the electric conductor 6 and the signal transmitting and receiving layer 8.

Figure 1:
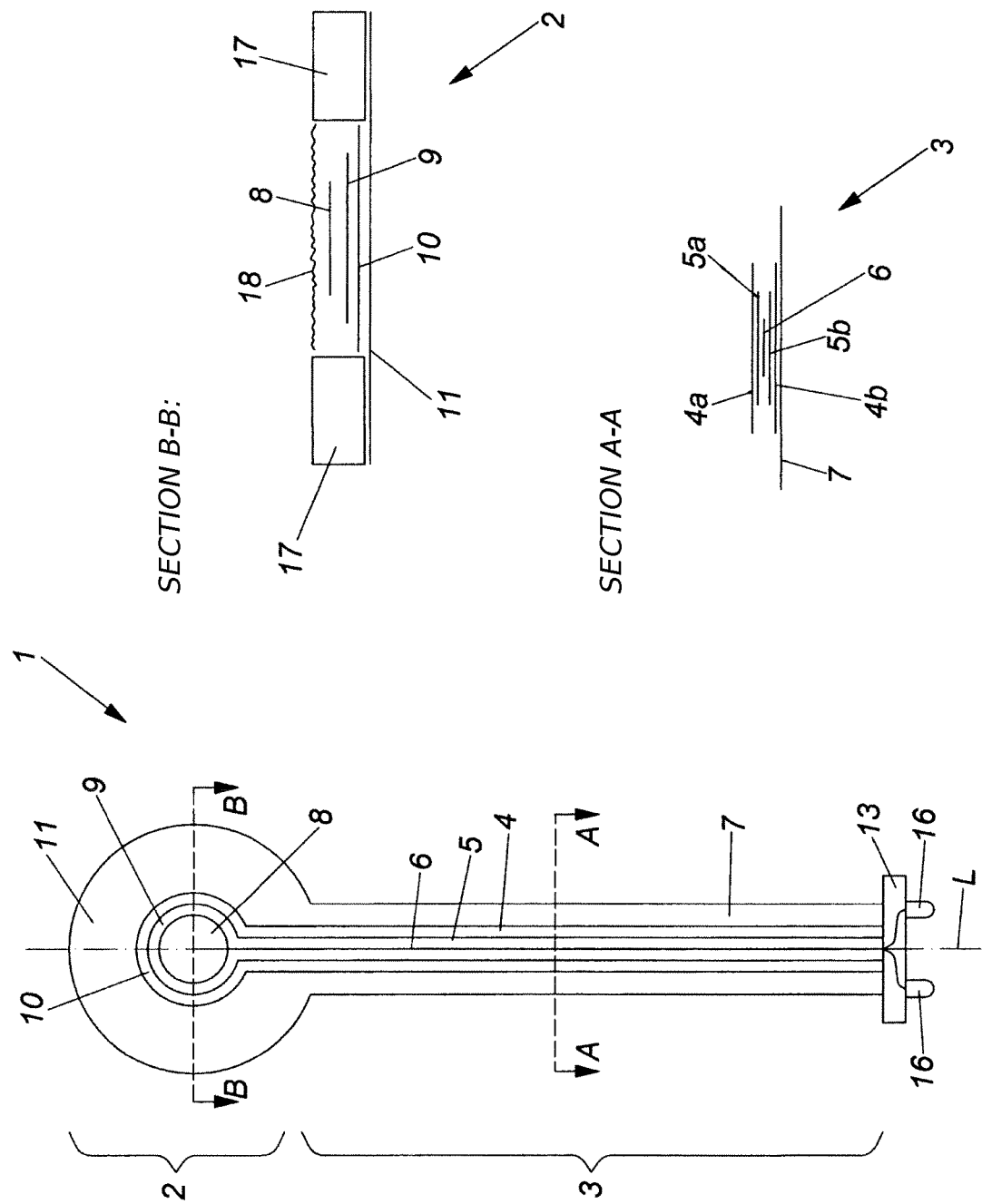
FIG. 1 is a schematic view of a medical electrode in the sections A-A and B-B.

A schematic cross-section in the region of the feed line 3 is shown in the section A-A, wherein firstly the lower shielding ply 4b and the lower dielectric element 5b are printed onto the substrate element 7. The upper dielectric element 5a and the upper shielding ply 4a are printed over the then applied electric conductor 6.

The essential components of the electrode head 2 can be seen schematically in cross-section in the section B-B, wherein the shielding layer 10, the dielectric element 9 and the signal transmitting and receiving layer 8 are printed onto the substrate element 11. In the lateral region these printed-on layers are bounded for example by a foamed material 17. To provide a better current conduction a gel 18 may be applied to the electrode head 2, as is known per se.

It should be noted in principle that in the drawings the interface between the electrode head 2 and feed line 3 is merely indicated. This interface where the electric conductor 6 is no longer covered by the upper dielectric element 5a or by the upper shielding ply 4a and can thus act without this protection as a signal transmitting and receiving layer 8, is described in words.

Figure 2:
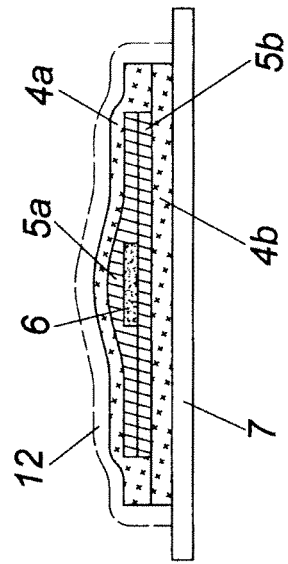
FIG. 2 is a cross-section through a feed line cable according to the prior art.

FIG. 2 shows in principle a section through a round shielded cable 23 already used in medical electrodes, with an electric conductor 6, a dielectric element 5, shielding 4 and optionally a protective sleeve 12.

Figure 3:
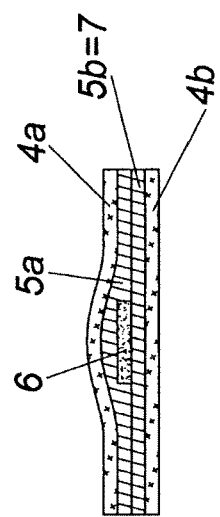
FIG. 3 is a cross-section through an embodiment of a feed line according to the invention.

Since in addition to the handling the fabrication in particular of such a known shielded cable 23 is relatively complicated and disadvantageous, according to the invention it is envisaged that the feed line 3 comprises an elongated substrate element 7 onto which at least a part of the electrically conductive shielding layer 4 is printed. A particularly preferred embodiment in this respect is shown in FIG. 3. In this case the lower shielding ply 4b is printed onto the substrate element 7 and the dielectric element 5b is printed on top of this. After the printing-on of the electric conductor 6 this is overprinted by the upper dielectric element 5a, whereby the electric conductor 6 is completely surrounded by the dielectric element 5 transverse to the longitudinal axis L, since the elements 5a and 5b are cohesively joined to one another at least over certain regions. The same also applies to the shielding plies 4a and 4b, which in turn completely surround the dielectric element 5 transverse to the longitudinal axis L. Furthermore a protective sleeve 12 can be applied for example by means of a lacquer spray, according to the dotted lines. It is also possible for the substrate element 7 and the lower shielding ply 4b to be designed in the form of a one-piece metalized film. The advantage of this is that only the upper shielding ply 4a has to be printed.

Figure 4:
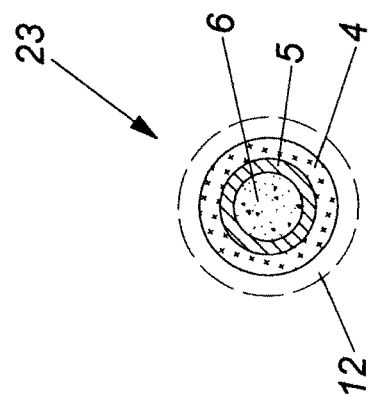
FIG. 4 is a cross-section through an alternative implementation of a feed line.

FIG. 4 shows an alternative embodiment of the present invention, in which no separate substrate element 7 is provided, but instead the lower dielectric element 5b is formed as substrate element 7.

In principle in all variants it should be possible that at least individual layers (4b, 5a, 5b and 6) are not applied in the printing method, but instead for example are also introduced as individual films between the other layers in the production process (e.g. in the form of an adhesive film or in the form of a wire).

Figure 5:
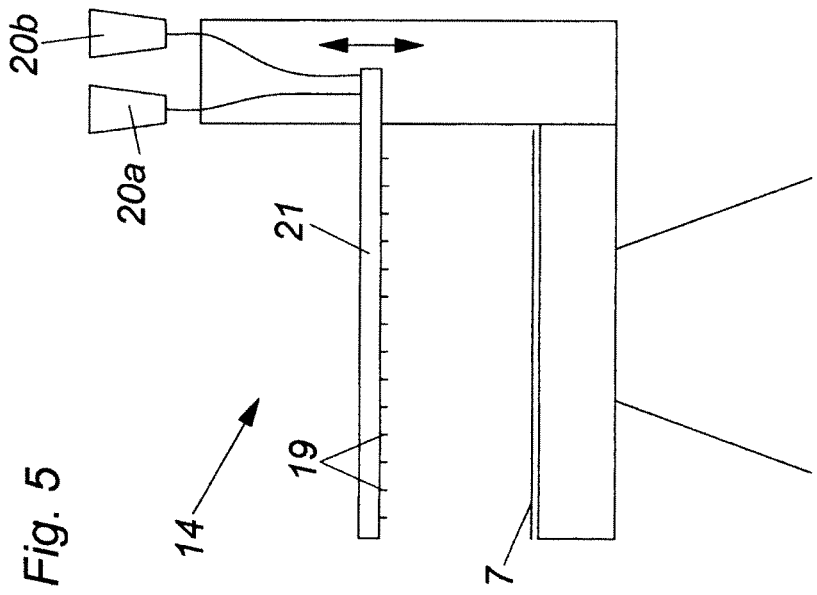
FIG. 5 shows schematically a printing device.

FIG. 5 shows schematically a printing device 14, with which at least individual layers of the medical electrode 1 can be printed. In principle it should be possible for the printing to take place in an in-line method or also by ink-jet printing. A screen-printing method is however preferred, in which a sheet up to several square meters in size, preferably in the form of a plastic substrate element 7, is fed into the printing device 14. The required basic components 20a and 20b are then applied to the substrate element 7 and onto previously extruded further layers 4, 5 or 6, via a moveable screen printing element 21 and via the printer nozzles 19. The desired final shapes of the feed line 3 and electrode head 2 are of course already taken into account in the printing, whereby as the simplest variant the feed line 3 is printed on as a straight, elongated element and the electrode head 2 is printed on as a relatively compact element.

Figure 6:
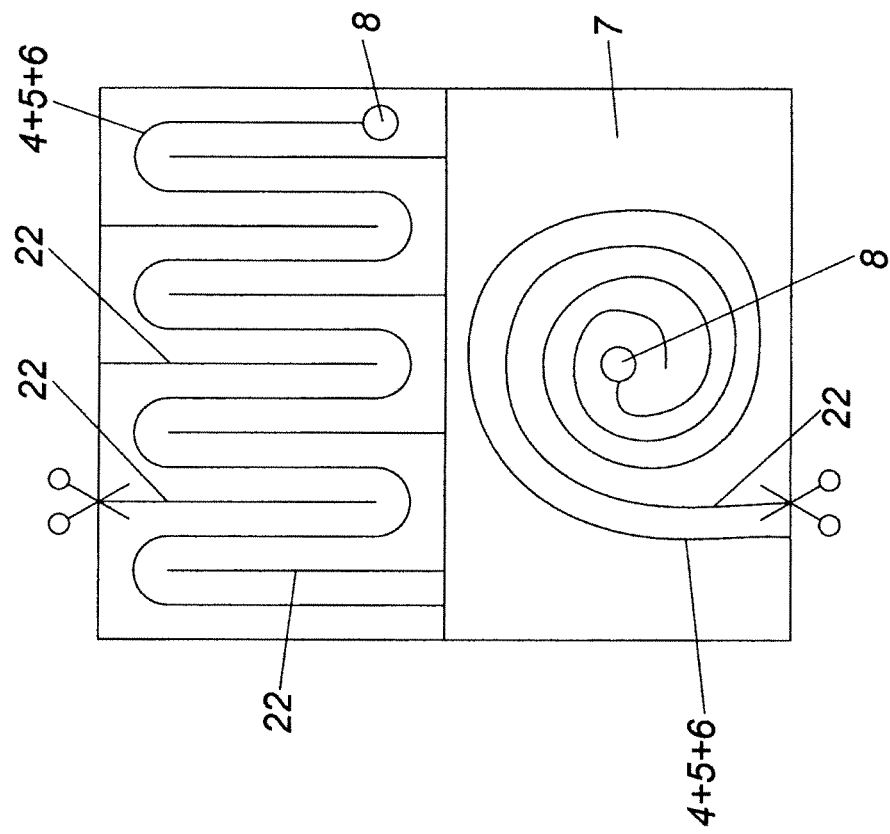
FIG. 6 is a plan view of a printed substrate element.

As an alternative a plan view of a substrate element 7 after the printing is shown in FIG. 6, wherein in the upper region a relatively long feed line cable 3 is printed with the layers 4, 5 and 6, wherein after the printed components have dried a relatively long feed line cable can be formed by means of a corresponding blank 22 cut out as illustrated by the shears. In a similar way and manner a spiral-shaped print and blank—as illustrated in the lower part of FIG. 6—can lead to a relatively long feed line cable 3. In principle however it is preferably envisaged that the feed line cable 3 is relatively straight and has a length between 30 and 150 cm, preferably between 50 and 100 cm.

Multiple electrodes 15 are illustrated in FIGS. 7 and 8, in which a plurality of separate layers 4, 5 and 6 and 8, 9 and 10 are applied to a substrate element 7 and 11.

An only very slightly extensible plastic material, such as for example a polyester (in particular PET), is preferably used as substrate element 7 and 11. It is however also possible to use a metalized film or even a polystyrene film as substrate element 7 and 11.

Carbo inks or metal inks (for example copper or silver inks) are used as shielding layer 4 and 10. These can be printed fully (over the whole surface) or in the manner of a grid.

In the printing method any suitable lacquer that is non-conductive and free from pores can be used as dielectric element 5 and 9.

The electric conductor 6 is produced, preferably printed, as a silver conductor. The signal receiving and transmitting layer 8 can also be applied in the form of a silver chloride layer. Tin and tin chloride can in principle also be used.

It should also be noted that in virtually all printed components 20a and 20b various additives such as lacquer elements, binders, solvents, etc are present, in order to ensure a frictionless printing procedure and to be able to produce functional layers that adhere well to one another.

Accordingly, the invention can be summarised as being based on replacing (shielded) feed line cables by a printed shielded feed line, wherein ideally this is produced (=printed) together with the electrode head (sensor region) in one production procedure. This has advantages especially as regards the subsequent assembly and installation. In particular the very complicated assembly of a plug integrating the shielding for the connection to the device, which is necessary in the case of shielded round cables, but also even in the hypothetical installation of such a cable on an electrode in the sense that a shielding element of the electrode would itself have to be electrically connected to the shielding of the cable, are radically simplified by the present invention.

The invention claimed is:

1. A medical electrode (1) with an electrode head (2) and an electric feed line (3) to the electrode head (2), wherein the feed line (3) comprises an electrically conductive shielding layer (4), a dielectric element (5) and an electric conductor (6), and wherein the feed line (3) comprises an elongated substrate element (7) onto which the electrically conductive shielding layer (4) is at least partly printed, characterised in that the at least partly printed shielding layer (4) entirely surrounds the dielectric element (5) and the electric conductor (6) transverse to the longitudinal axis (L) of the feed line (3), and wherein the at least partly printed shielding layer (4) comprises an upper shielding ply (4a) and a lower shielding ply (4b), wherein the upper shielding ply (4a) and the lower shielding ply (4b) are cohesively joined to one another.

2. The medical electrode according to claim 1, characterised in that the substrate element (7) is electrically non-conductive.

3. The medical electrode according to claim 2, characterised in that the dielectric element (5) and/or the electric conductor (6) are printed.

4. The medical electrode according to claim 2, characterised in that the shielding layer (4) is printed at least partly directly onto the substrate element (7) and the dielectric element (5) and the electric conductor (6) are printed indirectly onto the substrate element (7).

5. The medical electrode according to claim 1, characterised in that the dielectric element (5) and/or the electric conductor (6) are printed.

6. The medical electrode according to claim 5, characterised in that the shielding layer (4) is printed at least partly directly onto the substrate element (7) and the dielectric element (5) and the electric conductor (6) are printed indirectly onto the substrate element (7).

7. The medical electrode according to claim 1, characterised in that the shielding layer (4) is printed at least partly directly onto the substrate element (7) and the dielectric element (5) and the electric conductor (6) are printed indirectly onto the substrate element (7).

8. The medical electrode according to claim 1, characterised in that the feed line (3) comprises an upper (5a) and a lower (5b) dielectric element, which completely surrounds the electric conductor (6) transverse to the longitudinal axis (L) of the feed line (3).

9. The medical electrode according to claim 1, characterised in that the electrode head (2) comprises
- an electrically conductive signal transmitting and receiving layer (8) that is connected to the electric conductor (6) of the feed line (3),
- a dielectric element (9) that is connected to the dielectric element (5) of the feed line (3), and
- a shielding layer (10) that is connected to the shielding layer (4) of the feed line (3), wherein at least the electrically conductive signal transmitting and receiving layer (8) of the electrode head (2), the dielectric layer (9) of the electrode head (2) and/or the shielding layer (4) of the electrode head (2) are printed.

10. The medical electrode according to claim 9, characterised in that also the electrode head comprises an electrically non-conductive substrate element (11), wherein the shielding layer (10) of the electrode head (2) is printed directly onto the substrate element (11) of the electrode head (2).

11. The medical electrode according claim 1, characterised in that the elongated substrate element (7) forms at least one of the dielectric element (5) or a lower dielectric element (5b).

12. The medical electrode according to claim 1, characterised in that a protective layer (12) consisting of plastic material at least partly surrounds the electric feed line (3).

13. The medical electrode according to claim 1, characterised in that a connecting plug (13) is secured on the end of the feed line (3) remote from the electrode head, via which the medical electrode (1) is connected to at least one of a medical evaluation or a signal initiation unit.

14. The medical electrode according to claim 13, characterised in that the whole shielding layer (4), the whole dielectric element (5) and the whole electric conductor (6) is printed between the electrode head (2) and connecting plug (13).

* * * * *